United States Patent [19]

Umemura et al.

[11] 4,013,727
[45] Mar. 22, 1977

[54] PROCESS FOR PREPARING HYDROXYPHENYL ETHERS

[75] Inventors: Sumio Umemura; Nagaaki Takamitsu; Toshikazu Hamamoto; Nobuyuki Kuroda, all of Ube, Japan

[73] Assignee: UBE Industries, Ltd., Ube, Japan

[22] Filed: Oct. 20, 1975

[21] Appl. No.: 623,937

[30] Foreign Application Priority Data

Nov. 7, 1974 Japan .......................... 49-127515
Nov. 7, 1974 Japan .......................... 49-127516

[52] U.S. Cl. ........................ 260/613 R; 260/613 D
[51] Int. Cl.$^2$ ........................................ C07C 37/00
[58] Field of Search ........ 260/621 G, 613 D, 613 R

[56] References Cited
UNITED STATES PATENTS 3,003,000  10/1961  Milas .............................. 260/610
3,376,351  4/1968   Amedjian et al. ............. 260/613 D
3,849,502  11/1974  Bourdin et al. ................ 260/613 D

OTHER PUBLICATIONS

Kirk–Othmer, Encyclopedia of Chemical Technology, Second Edition, vol. 14, pp. 776–789 and 794–797.

*Primary Examiner*—Bernard Helfin
*Attorney, Agent, or Firm*—Flynn & Frishauf

[57]           ABSTRACT

A process for preparing hydroxyphenyl ethers by oxidizing phenyl ethers with hydrogen peroxide in the presence of a ketone or with a ketone peroxide.

16 Claims, No Drawings

PROCESS FOR PREPARING HYDROXYPHENYL ETHERS

This invention relates to a process for preparing hydroxyphenyl ethers. More particularly, this invention is concerned with a process for preparing hydroxyphenyl ethers having the formula (II):

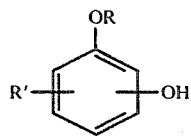
(II)

wherein R represents an alkyl radical or a phenyl radical and R' represents a hydrogen atom or an alkyl radical which comprises oxidizing phenyl ethers having the formula (I):

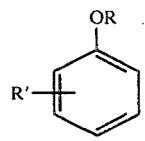
(I)

wherein R and R' have the same meanings as above with hydrogen peroxide in the presence of a ketone or with a ketone peroxide. As the previously known representative processes for preparing hydroxphenyl ethers by oxidizing phenyl ethers, there have been mentioned processes described in Japanese laid open specification Nos. 7234/1974, 62430/1974 and 66639/1974. The invention in the above specification of 7234/1974 relates to a process comprising oxidizing aromatic compounds in the presence of a Friedel-Craft catalyst such as aluminum chloride, boron fluoride and the like. Hydrogen peroxide must be used in an anhydrous state or particularly in a form of a urea-adduct, and a large amount of the catalyst is necessarily employed. Moreover, the catalyst cannot be recovered after reaction in the above process. Therefore, the above invention is not valuable industrially.

The inventions in the above specifications of Japanese laid open specification Nos. 62430/1974 and 66639/1974, which relate to processes comprising oxidizing aromatic compounds with hydrogen peroxide in the presence of formic acid, an inorganic acid such as pyrophosphoric acid and the like, or in the presence of phosphoric acid or its derivatives, respectively, are not satisfactory in the yield of hydroxyphenyl ethers.

It is, accordingly, an object of this invention to provide a process for preparing hydroxyphenyl ethers from phenyl ethers in a high yield based on the hydrogen peroxide or the ketone peroxide employed. Another object of this invention is to provide a process for preparing the desired compounds at a low cost. Still another object of this invention is to provide a reaction process wherein hydroxyphenyl ethers can be separated easily from the reaction mixture. Other objects and advantages of this invention are apparent from the descriptions of this specification.

This invention, as mentioned above, relates to a process for preparing hydroxyphenyl ethers having the formula (II) by oxidizing phenyl ethers having the formula (I) with hydrogen peroxide in the presence of a ketone or with a ketone peroxide,

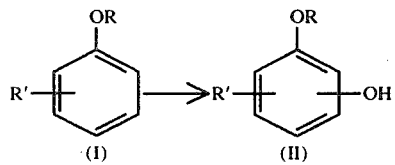

wherein R and R' have the same meanings as mentioned in the foregoing explanation.

According to the present process, hydroxyphenyl ethers can be produced in a higher yield than that in the prior processes, and the separation of the so produced hydroxyphenyl ethers from the reaction mixture can be easily accomplished, since the oxidizing agent, hydrogen peroxide is converted into water, and another oxidizing agent, a ketone peroxide is converted into water and a ketone. Moreover, the present process can be regarded as economical, since hydroxyphenyl ethers can be obtained in a high yield based on the hydrogen peroxide or the ketone peroxide employed.

Alkyl radicals, R and R' of phenyl ethers represented by the formula (I) used in principle in the process of the present invention are preferably straight or branched alkyl radicals having 1 – 4 carbon atoms.

As the starting phenyl ethers, there may be mentioned, for example, anisole, ethoxybenzene, propoxybenzene, butoxybenzene, secbutoxybenzene, tert-butoxybenzene, o-methoxytoluene, m-methoxytoluene, p-methoxytoluene, o-ethoxytoluene, m-ethoxytoluene, p-ethoxytoluene, p-propoxytoluene, butoxytoluene, diphenyl ether, phenoxytoluene and the like. As to the ketone which may be employed in conjunction with hydrogen peroxide in the present invention, there is no particular limitation. The following ketones may be mentioned.

1. A ketone having 3 – 20 carbon atoms and represented by the following general formula (III):

$$R_1 - CO - R_2 \quad \text{(III)}$$

wherein $R_1$ and $R_2$ may be the same or different and each represents a straight or branched alkyl group of 1 – 18 carbon atoms or phenyl group, the hydrogen of said alkyl groups being optionally substituted with a halogen atom, hydroxy group, amino group or phenyl group, and $R_1$ and/or $R_2$ may be an aliphatic group having an unsaturated bond;

2. a diketone having 3 – 20 carbon atoms and represented by the following general formula (IV):

$$R_1-\overset{O}{\underset{\|}{C}}-(CH_2)_n-\overset{O}{\underset{\|}{C}}-R_2 \quad \text{(IV)}$$

wherein $n$ is an integer of 0 – 16 inclusive, and $R_1$ and $R_2$ have the same meanings as above;

3. a cycloketone having the following general formula (V):

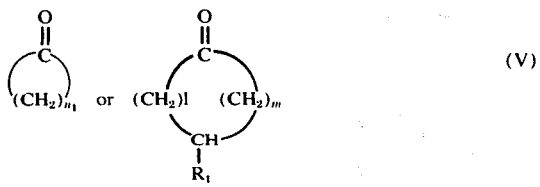 (V)

wherein $n_1$ represents an integer of 4 – 11, inclusive, $l + m$ represents an integer of 3 – 10, inclusive, and $R_1$ has the same meaning as above.

In the aliphatic ketone having the above-mentioned general formula (III), examples of the straight or branched alkyl groups of 1 – 18 carbon atoms in $R_1$ and $R_2$ are as follows:

Methyl, ethyl, propyl, 1-methylethyl, butyl, 1-methylpropyl, 1,1-dimethyl-ethyl, 2-methylpropyl, pentyl, 1-methylbutyl, 2-methylbutyl, 3-methylbutyl, 1,2-dimethylpropyl, hexyl, 1-methylpentyl, octyl, decyl, undecyl, 2-dodecyl, tridecyl, tetradecyl, pentadecyl, octadecyl, etc.

Representative examples of the ketones having the abovementioned alkyl groups are as follows:

Acetone, methylethylketone, 2-pentanone, 3-pentanone, 3-methyl-2-butanone, 2-hexanone, 3-hexanone, 3-methyl-2-pentanone, 4-methyl-2-pentanone, 3,3-dimethyl-2-butanone, 2-heptanone, 3-heptanone, 4-heptanone, 2,4-dimethyl-3-pentanone, 2-octanone, 6-methyl-2-heptanone, 2-nonanone, 2,6-dimethyl-4-heptanone, 2,2,4,4-tetramethyl-3-heptanone, 3-decanone, 6-undecanone, 2-tridecanone, 7-tridecanone, 2-tetradecanone, 2-pentadecanone, 2-hexadecanone, 2-heptadecanone, 3-octadecanone, 4-nonadecanone, 5-eicosanone, etc.

The unsaturated bond which the aliphatic ketones having the above-mentioned general formula (III) involve may be any double and triple bond, but a double bond is preferable.

As the ketones having an unsaturated bond may be mentioned the following: 3-buten-2-one, 3-penten-2-one, 5-hexen-2-one, 4-methyl-3-penten-2-one, 6-methyl-5-hepten-2-one, 5-octen-2-one, 7-nonadecen-2-one, etc.

Examples of the ketones having the above-mentioned general formula (III) which have a phenyl group or the alkyl groups substituted with a halogen atom, particularly a chlorine atom, bromine atom and hydroxy group, amino group and phenyl group are as follows: 1-chloro-2-propanone, 1-chloro-3-heptanone, 3-hydroxy-2-butanone, 1-bromo-3-heptanone, 1-hydroxy-2-propanone, 4-amino-4-methyl-2-pentanone, methylphenylketone, benzophenone, 1-phenyl-2-propanone, 1-phenyl-1-butanone, 1-phenyl-3-butanone, 1-phenyl-3-pentanone, 1,3-diphenyl-2-propanone, etc.

Examples of the diketones having the general formula (IV) are as follows: 2,3-butanedione, 2,4-pentanedione, 2,5-hexanedione, etc.

Examples of the cycloketones having the general formula (V) are as follows: cyclopentanone, cyclohexanone, 2-ethyl-1-cyclopentanone, 2-methyl-1-cyclohexanone, cyclododecanone, etc.

Particularly preferable ketones which may be employed in this invention are the $C_3 - C_{15}$ saturated aliphatic monoketone, the $C_5 - C_{12}$ saturated alicyclic monoketones and the aromatic monoketones, all of which have no substituents.

The ketone peroxide employed in the present invention, though it may be available commercially, is obtained according to the usual procedure, by the reaction of ketone with hydrogen peroxide or by the autoxidation of a secondary alcohol. The ketone peroxide possesses one or more of the following structures in the molecule.

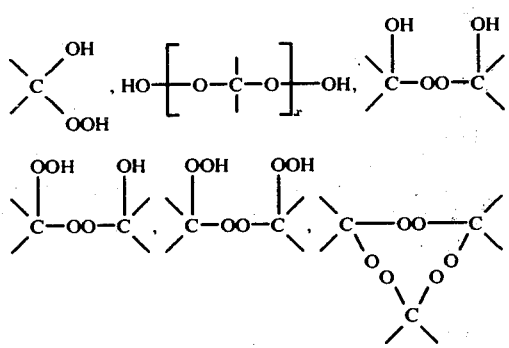

In the above formula, X represents an integer of 1 to 4.

In the above structures, the two bonds on a carbon atom may form a 5 or 6 membered ring in pairs.

Commercially available ketone peroxides may be used in this process. As shown in the Examples, they may be prepared by an usual method, for example, by reacting a ketone with hydrogen peroxide.

As to the ketone which may be employed for the purpose of preparing ketone peroxide there is no particular limitation. However, the above illustrated ketones may be used for that purpose.

And, the ketone peroxide can be easily produced through autoxidation of a secondary alcohol in a well-known manner.

As the secondary alcohol which may be employed in this invention may be any type of secondary alcohols and, for example, the following are mentioned.

1. A secondary alcohol having 3 – 20 carbon atoms are represented by the following general formula (VI):

 (VI)

wherein $R_1$ and $R_2$ have the same meanings as above;

2. a di-secondary alcohol having 3 – 20 carbon atoms and represented by the following general formula (VII):

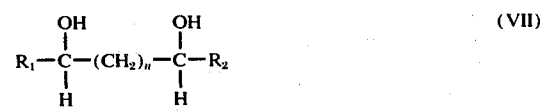 (VII)

wherein $R_1$, $R_2$ and n have the same meanings as above;

3. a cycloalcohol having the following general formula (VIII):

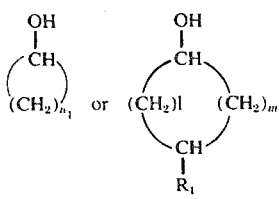

(VIII)

wherein $R_1$, $n_1$, $l$ and $m$ have the same meanings as above.

These secondary alcohols (VI), (VII) and (VIII) correspond to the ketones (III), (IV) and (V), respectively. Representative examples of such alcohols are given below.

As examples of those aliphatic secondary alcohols represented by the above-mentioned general formula (VI) wherein $R_1$ and $R_2$ are straight or branched alkyl groups of 1 – 18 carbon atoms may be mentioned the following: 2-propanol, 2-butanol, 2-pentanol, 3-pentanol, 3-methyl-2-butanol, 2-hexanol, 3-hexanol, 3-methyl-2-pentanol, 4-methyl-2-pentanol, 3,3-dimethyl-2-butanol, 2-heptanol, 3-heptanol, 4-heptanol, 2,4-dimethyl-3-pentanol, 2-octanol, 6-methyl-2-heptanol, 2-nonanol, 2,6-dimethyl-4-heptanol, 2,2,4,4-tetramethyl-3-pentanol, 3-decanol, 6-undecanol, 2-tridecanol, 7-tridecanol, 2-tetradecanol, 2-pentadecanol, 2-hexadecanol, 2-heptadecanol, 2-octadecanol, 3-octadecanol, 4-nonadecanol, 5-eicosanol, etc.

The unsaturated bond in the aliphatic secondary alcohol having the above-mentioned general formula (VI) may be any double and triple bond, but double bond is preferable. As the secondary alcohols having an unsaturated bond may be mentioned the following: 3-buten-2-ol, 3-penten-2-ol, 5-hexen-2-ol, 4-methyl-3-penten-2-ol, 6-methyl-5-hepten-2-ol, 5-octen-2-ol, 7-nonadecen-2-ol, etc.

As examples of the secondary alcohols having the above-mentioned general formula (VI) wherein $R_1$ and $R_2$ are phenyl groups or alkyl groups substituted with a halogen atom, particularly a chlorine atom and bromine a atom, hydroxy groups, amino group and phenyl group may be mentioned the following: 1-chloro-2-butanol, 1-chloro-3-heptanol, 3-hydroxy-2-butanol, 1-bromo-3-heptanol, 1-hydroxy-2-propanol, 4-amino-4-methyl-2-pentanol, 1-phenylethanol, diphenylmethanol, 1-phenyl-2-propanol, 1-phenyl-1-butanol, 1-phenyl-3-butanol, 1-phenyl-3-pentanol, 1,3-diphenyl-2-propanol, etc.

As examples of the secondary dihydric alcohols having the above-mentioned general formula (VII) may be mentioned the following: 2,3-butanediol, 2,4-pentanediol, 2,5-hexanediol, etc.

As examples of the secondary alcohols having the above-mentioned general formula (VIII) may be mentioned the following: cyclopentanol, cyclohexanol, 2-ethyl-1-cyclopentanol, 2-methyl-1-cyclohexanol, etc.

Particularly preferable ketones and alcohols which may be employed in this invention are the $C_3 - C_{15}$ saturated aliphatic monoketones and monoalcohols, the $C_5 - C_{12}$ saturated alicyclic monoketones and monoalcohols and the aromatic monoketones and monoalcohols, all of which have no substituents.

The oxidation of phenyl ethers with hydrogen peroxide in the presence of the above mentioned ketones is effected under the following conditions.

Concentration of the hydrogen peroxide employed is not particularly critical. But, the oxidation reaction is promoted and the desired hydroxyphenyl ether is obtained in a high yield, when the reaction is carried out in the presence of as little water as possible. Accordingly, more than 60% hydrogen peroxide is advantageously employed, although 30 – 60% commercially available hydrogen peroxide also can be used.

The water in the reaction system may be diminished according to well-known procedures, for example, by distilling off the water alone or as an azeotropic mixture with phenyl ether, ketone or other solvents out of the reaction system, said water being contained in the hydrogen peroxide employed or being generated as a result of the reaction.

The amount of ketone used may be small, but there is no critical upper limit of the amount used since excess ketone may also act as a reaction solvent. The particularly preferred amount of ketone to hydrogen peroxide is a molar ratio of 0.005 – 20. The molar ratio of the hydrogen peroxide used to phenyl a ether is not particularly critical, but the preferable molar ratio is 0.005 – 0.5. The oxidation reaction with hydrogen peroxide is conducted at a temperature of 20° – 250° C., preferably 80° – 200° C. A solvent may not be used, but, if used, there may be used those solvents that could not prevent oxidation reaction, such as methyl acetate, ethyl acetate, ethylene diacetate, etc. As mentioned above, the ketone, if used in excess, serves as a solvent. A solvent is necessarily employed, in case the reaction is conducted at a temperature below the melting point of the phenyl ether.

The oxidation of phenyl ethers with a ketone peroxide is effected under the following conditions.

The amount of the ketone peroxide employed is not particularly critical, but the peroxide amount P per m.mole of a phenyl ether is a value 0.005 – 1.00, preferably 0.01 – 0.50. The above-mentioned peroxide amount "P" is expressed by the following equation:

$$P = \frac{a \times b \times 10}{16}$$

$a$: active oxygen amount (%)
$b$: ketone peroxide weight (g.)

The term "active oxygen" as used herein is meant to indicate one oxygen atom in the oxygens constituting a peroxide bond —O.O— and said oxygen atom is capable of effecting the following reactions when the corresponding peroxide is added to hydrochloric acid — potassium iodide or acetic acid—potassium iodide.

$$2KI + 2HCl + O \rightarrow I_2 + 2KCl + H_2O \quad (a)$$

$$2KI + 2CH_3COOH + O \rightarrow I_2 + 2CH_3COOK + H_2O \quad (b)$$

The term "active oxygen amount" as used herein is meant to be a weight percentage of the active oxygen contained in a sample peroxide and its determination is done by making a peroxide participate in the above reaction (a) or (b) and measuring the iodine so liberated iodine.

The oxidation reaction with ketone peroxide is conducted at a temperature of 20° – 250° C., preferably 80° – 200° C. A solvent may not be used, but, if used there may be used those solvents that could not prevent oxidation reaction, such as methyl acetate, ethyl acetate, ethylene diacetate, methyl benzoate, dimethyl phthalate, diethyl phthalate, benzene, etc. as well as various ketones such as acetone, methyl ethyl ketone, 2-pentanone, 3-pentanone, 3-methyl-2-butanone, 2-hexanone, 3-hexanone, 4-methyl-2-pentanone, 3,3-dimethyl-2-butanone, cyclopentanone, methyl phenyl ketone, etc. For improved yield of hydroxyphenyl ethers, a water content in the reaction system should be desirably as low as possible.

In the present invention, the reaction period may vary upon the reaction temperature and upon the presence and amount of a catalyst as set forth below.

The present reaction may be effected without any use of a catalyst, but the reaction is preferably conducted in the presence of a catalyst as stated below. The catalysts which may be employed in the present reaction are activated clay, boric acids or boric acid derivatives. As boric acids and boric acid derivatives, are exemplified orthoboric acid, metaboric acid, tetraboric acid and boron oxide. The amount of the catalyst may vary in a wide range. But, the amount is preferably not less than 0.001 weight percent based on the phenyl ether employed to carry out the reaction with a sufficient reaction rate. In the foregoing, a batchwise practice of the present reaction was illustrated, but it is to be noted that a continuous reaction of the present invention may be also practised. More specifically, there may be mentioned a process wherein a stock flow is continuously supplied to a catalyst layer for reaction, a process wherein a catalyst is suspended or dissolved in a stock flow and the resultant is passed through a reaction zone and so forth. In the latter case, the required amount of a catalyst may be determined according to the batchwise system.

For separation of the desired product after completion of the reaction, well-known procedures may be applied, as the present reaction does not involve any matters to prevent the desired product from separation. For example, the desired product may be easily separated by subjecting the reaction mixture to distillation, in many cases after cooling of the reaction mixture and removal of the catalyst. Namely, water, the ketone, phenyl ethers and the hydroxyphenyl ethers so produced may be optionally subjected to fractional distillation. The so separated ketone and phenyl ethers may be circulated for reuse in the next reaction.

The hydroxyphenyl ethers so produced may be obtained either in substantially one type or in a mixture of several types, depending upon the structure of the starting phenyl ethers.

For instance, where anisole is employed as a starting material, a mixture of o-methoxyphenol and p-methoxyphenol is formed. Where ethoxybenzene is employed as a starting material, a mixture of o-ethoxyphenol and p-ethoxyphenol is formed. Where o-methoxytoluene is employed as a starting material, a mixture of 2-methoxy-3-methylphenol and 4-methoxy-3-methylphenol is formed. Where m-methoxytoluene is employed as a starting material, a mixture of 2-methoxy-4-methylphenol, 2-methoxy-6-methylphenol and 4-methoxy-2-methylphenol is formed. Where p-methoxytoluene is employed as a starting material, 2-methoxy-5-methylphenol is formed. As illustrated by the above examples, all the hydroxyl groups introduced by oxidation are at an ortho- or para-position to the ether group of a phenyl ether represented by the formula (I).

The so obtained hydroxyphenyl ether may be utilized, for example, for an intermediate for the production of a dyestuff and drug, and an antioxidant as a single product or, if obtained in the form of a mixture, as a mixture as such or after separation if desired.

The process of this invention is more concretely illustrated by way of the following examples, but these examples are not limiting the process of this invention.

The ketone peroxide which is employed in the following examples is the same as defined below or produced in the same manner as shown below.

METHOD FOR THE SYNTHESIS OF A KETONE PEROXIDE

1. Methyl ethyl ketone peroxide (manufactured by Nihon Yushi K. K., Permec N)

A 55 % by weight solution of methyl ethyl ketone peroxide dissolved in dimethyl phthalate. Active oxygen amount: 17.5 %.

2. 4-Methyl-2-pentanone peroxide (synthesized)

To a stirred mixture of 45 g. (0.397 mole) of 30% hydrogen peroxide solution and 28.8 g. of 100% $H_3PO_4$ is added 27.7 g. (0.277 mole) of 4-methyl-2-pentanone at 20° – 25° C. and, after stirring for about 10 minutes, the mixture is allowed to stand. A peroxide layer is separated, neutralized with calcium carbonate and filtered. The unchanged ketone is removed by distillation in vacuo and the remainder is used as an oxidizing reagent. Active oxygen amount: 16.9%.

3. Methylphenyl ketone peroxide (synthesized)

This peroxide is synthesized in the same manner as in the above (2) except that 33.2 g. (0.277 mole) of methyl phenyl ketone is employed instead of the 4-methyl-2-pentanone providing that the unchanged ketone is not distilled off. Active oxygen amount: 3.73%.

EXAMPLE 1

Into a flask equipped with a stirrer, a thermometer, an inlet for liquid and a downward condenser, were introduced 150 g. (1388.9 m.moles) of anisole, 4.51 g. (45.1 m.moles) of 4-methyl-2-pentanone, 2.53 g. (44.6 m.moles) of 60% hydrogen peroxide and 540 g. of ethyl acetate. The flask was dipped in an oil bath of 80° C. With stirring the reaction mixture, ethyl acetate and water were distilled off.

Subsequently, the downward condenser was replaced by a reflux condenser and the temperature of the oil bath was raised up to 160° C.

The reaction mixture was stirred for 200 minutes and analyzed thereafter by gas chromatography to give 0.805 g. (6.49 m.moles) of o-methoxyphenol and 0.573 g. (4.62 m.moles) of p-methoxyphenol. The yield was defined as follows:

$$\text{Yield of hydroxyphenyl ethers (\%)} = \frac{\text{m.mole number of hydroxyphenyl ethers produced}}{\text{m.mole number of hydrogen peroxide charged}} \times 100$$

The yield of the above hydroxyphenyl ethers was 24.9 %.

COMPARATIVE EXAMPLE

The reaction and analysis were carried out in the same manner as in Example 1 except that 4-methyl-2-pentanone was not added, to give 0.465 g. (3.75 m.moles) of o-methoxyphenol and 0.324 g. (2.61 m.moles) of p-methoxyphenol. The yield of the hydroxyphenyl ethers was 14.3 %.

EXAMPLE 2

Into a flask equipped with a stirrer, a thermometer, an inlet for liquid and a downward condenser, were introduced 150 g. (1388.9 m.moles) of anisole, 4.50 g. (45.0 m.moles) of 4-methyl-2-pentanone, 2.84 g. (50.1 m.moles) of 60% hydrogen peroxide, 2.1 g. of activated clay (manufactured by Mizusawa Kagaku K.K., Activated clay H) and 540 g. of ethyl acetate. The flask was heated up to 80° C in an oil bath to remove ethyl acetate and water while stirring the reaction mixture. Subsequently, the downward condenser was replaced by a reflux condenser. The temperature of the oil bath was raised up to 120° C and the reaction was continued for 20 minutes.

Analysis as in Example 1, showed that 2.10 g. (16.9 m.moles) of o-methoxyphenol and 2.05 g. (16.5 m.moles) of p-methoxyphenol were yielded. The yield of these hydroxyphenyl ethers was 66.7%.

EXAMPLE 3

Into the flask mentioned above, were introduced 150 g. (1388.9 m.moles) of anisole, 6.10 g. (50.8 m.moles) of methyl phenyl ketone, 3.24 g. (57.2 m.moles) of 60% hydrogen peroxide, 2.1 g. of activated clay (manufactured by Mizusawa Kagaku K. K., Activated clay H) and 540 g. of ethyl acetate.

After evaporation of ethyl acetate and water, the reaction was carried out at 140° C for 10 minutes to give 2.24 g. (18.1 m.moles) of o-methoxyphenol and 2.21 g. (17.8 m.moles) of p-methoxyphenol. The yield of these hydroxyphenyl ethers was 62.8%.

EXAMPLE 4

Into the flask mentioned above, were introduced 150 g. (1388.9 m.moles) of anisole, 4.50 g. (45.0 m.moles) of 4-methyl-2-pentanone, 4.01 g. (70.8 m.moles) of 60% hydrogen peroxide, 1.1 g. of orthoboric acid and 540 g. of ethyl acetate. After distilling off ethyl acetate and water in the same manner as in Example 2, the reaction was carried out at 120° C for 20 minutes to give 2.65 g. (21.4 m.moles) of o-methoxyphenol and 1.82 g. (14.7 m.moles) of p-methoxyphenol. The yield of these hydroxyphenyl ethers was 51.0%.

EXAMPLE 5

The reaction was carried out in the same manner as in Example 4 except that orthoboric acid was replaced by 1.2 g. of anhydrous boric acid and 2.60 g. (21.0 m.moles) of o-methoxyphenol and 1.74 g. (14.0 m.moles) of p-methoxyphenol were obtained. The yield of these hydroxyphenyl ethers was 49.4%.

EXAMPLE 6

Into the flask mentioned in Example 2, were introduced 150 g. (1229.5 m.moles) of ethoxybenzene, 4.50 g. (45.0 m.moles) of 4-methyl-2-pentanone, 3.60 g. (63.5 m.moles) of 60% hydrogen peroxide, 0.070 g. of activated clay (manufactured by Mizusawa Kagaku K. K., Activated clay VH) and 540 g. of ethyl acetate. After removing ethyl acetate and water, the reaction was carried out at 140° C for 30 minutes to give 2.74 g. (19.9 m.moles) of o-ethoxyphenol and 3.20 g. (23.2 m.moles) of p-ethoxyphenol. The yield of these hydroxyphenyl ethers was 67.9%.

EXAMPLE 7

The reaction was carried out in the same manner as in Example 6 except that ethoxybenzene was replaced by 150 g. (1229.5 m.moles) of p-methoxytoluene and 4.11 g. (29.8 m.moles) of 2-methoxy-5-methylphenol was obtained in a yield of 46.9%.

EXAMPLE 8

Into a flask equipped with a stirrer, a thermometer, an inlet for liquid and a downward condenser, were introduced 1500 g. (13.89 moles) of anisole, 10 g. (0.10 mole) of 4-methyl-2-pentanone, 29.8 g. (0.53 mole) of 60% hydrogen peroxide, 12 g. of activated clay (manufactured by Mizusawa Kagaku K. K.) and 5600 g. of ethyl acetate. The flask was heated up to 80° C in an oil bath to distill off ethyl acetate and water while stirring of the reaction mixture. After the downward condenser was replaced with a reflux condenser, the temperature of the oil bath was raised to 130° C and the reaction was continued for 20 minutes with stirring. The reaction mixture was cooled to room temperature. After removing the catalyst by filtration, the reaction mixture was fractionated to give 22.3 g. (0.18 mole) of o-methoxyphenol and 21.3 g. (0.17 mole) of p-methoxyphenol. The yield of these hydroxyphenyl ethers was 66.0%.

EXAMPLE 9

In a 300-ml. four necked flask equipped with a reflux condenser, a thermometer, a stirrer and an outlet for liquid was placed 150 g. (1388.9 m.moles) of anisole and 4.31 g. (P = 45.5) of 4-methyl-2-pentanone peroxide. The flask was dipped in an oil bath of 160° C and the mixture was subjected to reaction with stirring for 200 minutes. The reaction mixture was analyzed by gas chromatography to give 0.818 g. (6.60 m.moles) of o-methoxyphenol and 0.592 g. (4.78 m.moles) of p-methoxyphenol.

According to the formula defined below, the yield of these hydroxyphenyl ethers was 25.0% based on the peroxide employed.

Yield of hydroxyphenyl ethers (%)

$$= \frac{\text{m.mole number of hydroxyphenyl ethers produced}}{\text{amount of peroxide charged } (P)} \times 100$$

EXAMPLE 10

In the flask mentioned above were placed 150 g. (1388.9 m.moles) of anisole, 4.31 g. (P = 45.5) of 4-methyl-2-pentanone peroxide and 1.3 g. of activated clay (manufactured by Mizusawa Kagaku K. K., Activated clay H). The mixture was subjected to reaction at 120° C for 20 minutes and analyzed thereafter in the same manner as in Example 9 to give 2.10 g. (16.9 m.moles) of o-methoxyphenol and 1.62 g. (13.1 m.moles) of p-methoxyphenol. The yield of these hydroxyphenyl esters was 65.9%.

EXAMPLE 11

In the flask mentioned above were introduced 150 g. (1388.9 m.moles) of anisole, 12.7 g. (P = 138.9) of methyl ethyl ketone peroxide and 1.2 g. of activated clay (manufactured by Mizusawa Kagaku K. K., Activated clay H). The mixture was subjected to reaction at 90° C for 60 minutes in the same manner as in Example 9 to give 5.53 g. (44.6 m.moles) of o-methoxyphenol and 4.34 g. (35.0 m.moles) of p-methoxyphenol. The yield of these hydroxyphenyl esters was 57.3%.

EXAMPLE 12

In the flask mentioned above were placed 150 g. (1388.9 m.moles) of anisole, 19.9 g. (P = 46.4) of methyl phenyl ketone peroxide and 1.20 g. of activated clay (manufactured by Mizusawa Kagaku K. K., Activated clay VH). The mixture was subjected to reaction at 120° C for 20 minutes in the same manner as in Example 9 to give 2.17 g. (17.5 m.moles) of o-methoxyphenol and 1.44 g. (11.6 m.moles) of p-methoxyphenol. The yield of these hyroxyphenyl ethers was 62.7%.

EXAMPLE 13

In the flask mentioned above were placed 150 g. (1388.9 m.moles) of anisole, 6.57 g. (P = 69.4) of 4-methyl-2-pentanone peroxide and 1.10 g. of orthoboric acid. The mixture was subjected to reaction at 100° C for 30 minutes in the same manner as in Example 9 to give 2.78 g. (22.4 m.moles) of o-methoxyphenol and 1.86 g. (15.0 m.moles) of p-methoxyphenol. The yield of these hydroxyphenyl ethers was 53.9%.

EXAMPLE 14

In the flask mentioned above were placed 150 g. (1388.9 m.moles) of anisole, 6.57 g. (P = 69.4) of 4-methyl-2-pentanone peroxide and 1.20 g. of boric anhydride. The mixture was subjected to reaction at 120° C for 20 minutes in the same manner as in Example 9 to give 2.71 g. (21.9 m.moles) of o-methoxyphenol and 1.67 g. (13.5 m.moles) of p-methoxyphenol. The yield of these hydroxyphenyl ethers was 51.0%.

EXAMPLE 15

In the flask mentioned above were placed 150 g. (1229.5 m.moles) of ethoxybenzene, 5.97 g. (P = 63.1) of 4-methyl-2-pentanone peroxide and 1.16 g. of activated clay (manufactured by Mizusawa Kagaku K. K., Activated clay VH). The mixture was subjected to reaction at 140° C for 10 minutes in the same manner as in Example 9 to give 3.17 g. (23.0 m.moles) of o-ethoxyphenol and 2.35 g. (17.0 m.moles) of p-ethoxyphenol. The yield of these hydroxyphenyl ethers was 63.4%.

EXAMPLE 16

In the flask mentioned above were placed 150 g. (1229.5 m.moles) of p-methoxytoluene, 6.05 g. (P = 63.9) of 4-methyl-2-pentanone peroxide and 0.091 g. of activated clay (manufactured by Mizusawa Kagaku K. K., Activated clay H). The mixture was subjected to reaction at 140° C for 15 minutes in the same manner as in Example 9 to give 4.09 g. (29.6 m.moles) of 2-methoxy-5-methylphenol. Yield: 46.4%.

EXAMPLE 17

Into a 3-l. flask equipped with a reflux condenser, a thermometer, a stirrer and an outlet for liquid were introduced 1500 g. (13.89 moles) of anisole, 43.1 g. (P = 455) of 4-methyl-2-pentanone peroxide and 10 g. of activated clay (manufactured by Mizusawa Kagaku K. K., Activated clay H). The mixture was heated to 140° C in an oil bath and subjected to reaction for 10 minutes with stirring. In the next step, the reaction mixture was cooled to room temperature and the catalyst was removed by filtration. The filtrate was distilled to give 20.5 g. (0.165 mole) of o-methoxyphenol and 15.9 g. (0.128 mole) of p-methoxyphenol. The yield of these hydroxyphenyl ethers was 64.4%.

What is claimed is:
1. A process for preparing a hydroxyphenyl ether having the formula:

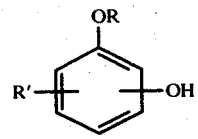

wherein R represents an alkyl radical or a phenyl radical and R' represents a hydrogen atom or an alkyl radical, which comprises oxidizing a phenyl ether having the formula:

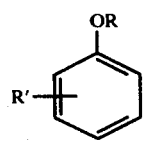

wherein R and R' have the same meanings as above, with hydrogen peroxide in the presence of a ketone, or with a ketone peroxide, at a temperature of 20° to 250° C. in the presence of a catalyst selected from the group consisting of an activated clay, a boric acid or a boric acid derivative, the amount of catalyst being more than 0.001 weight percent of said phenyl ether, said ketone being selected from the group consisting of (i) through (iii) following:
  i. a ketone having from 3 to 20 carbon atoms and represented by the following formula:

wherein $R_1$ and $R_2$ may be the same or different and each represents a straight or branched alkyl group of 1 - 18 carbon atoms or phenyl group, and either $R_1$ or $R_2$ may be an aliphatic group having an unsaturated bond;
  ii. a diketone having from 3 to 20 carbon atoms and represented by the following formula:

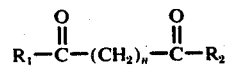

wherein $n$ is an integer of from 0 to 16, inclusive, and $R_1$ and $R_2$ have the same meanings as above;
  iii. a cycloketone having the following formula:

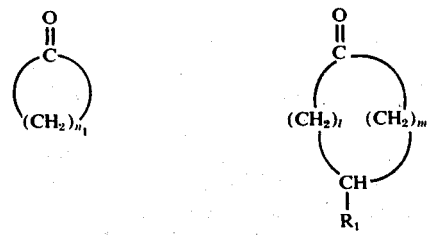

wherein $n_1$ represents an integer of from 4 to 11, inclusive, $l + m$ represents an integer of from 3 to 10, inclusive, and $R_1$ has the same meaning as above; and said ketone peroxide being obtained by reaction of hydrogen peroxide and a ketone selected from the group of said (i) to (iii) or derived from a secondary alcohol selected from the group consisting of a secondary alcohol having the following formula:

iv. a secondary alcohol having from 3 to 20 carbon atoms and represented by the following formula:

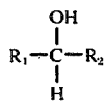

wherein $R_1$ and $R_2$ have the same meanings as above;

v. a di-secondary alcohol having from 3 to 20 carbon atoms and represented by the following formula:

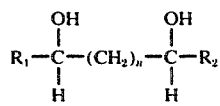

wherein $R_1$, $R_2$ and $n$ have the same meanings as above; and vi. a cycloalcohol having the following formula:

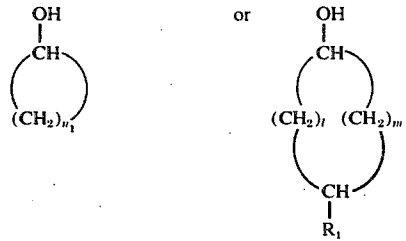

wherein $R_1$, $n_1$, $l$ and $m$ have the same meanings as above.

2. The process for preparing a hydroxyphenyl ether as claimed in claim 1 which comprises oxidizing the phenyl ether with hydrogen peroxide in the presence of a ketone.

3. The process for preparing a hydroxyphenyl ether as claimed in claim 1 which comprises oxidizing the phenyl ether with a ketone peroxide.

4. The process as claimed in claim 2 in which the ketone is a ketone selected from the group consisting of a saturated aliphatic monoketone having 3 – 15 carbon atoms, a saturated alicyclic monoketone having 5 – 12 carbon atoms and an aromatic ketone, each of which is unsubstituted.

5. The process as claimed in claim 2 in which the oxidation of the phenyl ether is conducted by using hydrogen peroxide in a 0.005 – 0.5 molar ratio to the phenyl ether, and the ketone in a 0.005 – 20 molar ratio to hydrogen peroxide.

6. The process as claimed in claim 1 in which the oxidation of the phenyl ether is conducted at a temperature of 80° – 200° C.

7. The process as claimed in claim 3 in which the ketone peroxide is derived from a ketone selected from the group consisting of a saturated aliphatic monoketone having 3 – 15 carbon atoms, a saturated alicyclic monoketone having 5 – 12 carbon atoms and an aromatic monoketone.

8. The process as claimed in claim 3 in which the ketone peroxide is derived by the autoxidation of a secondary alcohol selected from the group consisting of a saturated monoalcohol having 3 – 15 carbon atoms, a saturated alicyclic monoalcohol having 5 – 12 carbon atoms and an aromatic monoalcohol.

9. The process as claimed in claim 3 in which the oxidation of a phenyl ether is conducted by using a ketone peroxide in an amount of 0.005 – 1.00 m. atom number of active oxygen contained in the ketone peroxide per m. mole number of phenyl ether.

10. The process as claimed in claim 3 in which the oxidation of the phenyl ether is conducted at a temperature of 80° – 200° C.

11. The process as claimed in claim 1, wherein the catalyst is an activated clay.

12. The process as claimed in claim 1, wherein the catalyst is orthoboric acid.

13. The process as claimed in claim 1, wherein the catalyst is boric anhydride.

14. The process as claimed in claim 1, wherein the catalyst is boric acid.

15. The process as claimed in claim 1, wherein R has from 1 to 4 carbon atoms.

16. The process as claimed in claim 1, wherein R' has from 1 to 4 carbon atoms.

* * * * *